United States Patent [19]

Kilbane, II

[11] Patent Number: 5,750,065
[45] Date of Patent: May 12, 1998

[54] ADSORPTION OF PCB'S USING BIOSORBENTS

[75] Inventor: John J. Kilbane, II, Woodstock, Ill.

[73] Assignee: Institute of Gas Technology, Des Plaines, Ill.

[21] Appl. No.: 8,212

[22] Filed: Jan. 25, 1993

[51] Int. Cl.⁶ .................................................. B29B 17/00
[52] U.S. Cl. .................... 264/344; 420/590; 570/216; 570/181
[58] Field of Search .................... 436/537, 54, 825; 435/7.9, 177, 180, 181, 183, 814, 817, 962; 530/810, 816, 8; 536/124, 127; 264/344; 420/590; 570/181, 216

[56] References Cited

U.S. PATENT DOCUMENTS

| | | |
|---|---|---|
| 4,230,053 | 10/1980 | Deardorff et al. . |
| 4,246,351 | 1/1981 | Miyake et al. . |
| 4,276,179 | 6/1981 | Soehngen . |
| 4,629,785 | 12/1986 | McCaffery, III . |
| 4,981,961 | 1/1991 | Ngo ........................................ 536/112 |
| 5,028,657 | 7/1991 | Hsu et al. . |
| 5,089,470 | 2/1992 | Jackson et al. . |
| 5,093,254 | 3/1992 | Giuliano et al. . |
| 5,110,733 | 5/1992 | Kim et al. . |
| 5,110,833 | 5/1992 | Mosbach ................................. 521/50 |
| 5,145,790 | 9/1992 | Mattingly et al. ..................... 436/536 |

OTHER PUBLICATIONS

Dabulis K et al, "Molecular Imprinting of Proteins and Other Macromolecules Resulting in New Adsorbents", Biotechnology and Bioengineering, vol. 39, pp. 176–185 (1992). John Wiley & Sons, Inc.

*Primary Examiner*—Merrick Dixon
*Attorney, Agent, or Firm*—Speckman Pauley Petersen & Fejer

[57] ABSTRACT

A method for producing biosorbents for adsorption of PCB's in which at least one proteinaceous material is contacted with a molar excess of at least one PCB congener mixture, forming a protein/PCB congener mixture. The protein/PCB congener mixture is dried after which the PCB congeners are extracted from the dried protein/PCB congener mixture forming a biosorbent in the form of an imprinted protein.

9 Claims, No Drawings

ADSORPTION OF PCB'S USING BIOSORBENTS

BACKGROUND OF THE INVENTION

1. Field of the Invention

This invention relates to a method for producing biosorbents for selective adsorption of PCB's and the use of such biosorbents for removal of PCB's from PCB-contaminated environments. In particular, this invention relates to a method for imprinting proteins to selectively adsorb PCB's from PCB-contaminated oils. There are a possible 209 PCB congeners in a PCB mixture. This invention also provides a method for imprinting proteins to selectively adsorb all of the PCB congeners present in a PCB mixture. As used throughout the specification and claims, the term "PCB" refers to one or more of the possible 209 PCB congeners.

2. Description Of The Prior Art

Polychlorinated biphenyls (PCB's) are found in a variety of oils, including natural gas distribution pipeline oils, and environmental regulations have mandated the removal of these pollutants. However, known methods for disposal of PCB's in oils, such as thermal destruction in an incinerator, usually involve destruction of the oils themselves as well as the PCB's and are expensive to operate. Thus, an inexpensive means for selectively adsorbing PCB's would solve many PCB contamination problems.

Various methods of separation or extraction of various molecular compounds are taught by the prior art. U.S. Pat. No. 5,110,733 teaches a method of separating and purifying a variety of substances, in particular, biologically active materials, using liquid—liquid extraction in aqueous systems. U.S. Pat. No. 5,028,657 teaches a method of immobilizing proteins on a polymeric matrix using plasma in which the protein mixture is applied to the surface of the polymeric matrix and placed in a plasma generator in which the functional groups on the protein and matrix molecules are activated to form free radicals which, in turn, form covalent bonds between the proteins and between the protein and the polymeric matrix. U.S. Pat. No. 4,246,351 teaches a method of adsorbing a protein from an aqueous solution in which the aqueous solution is contacted with a porous copolymer obtained by copolymerization of a monomer mixture comprising 2% to 98% by weight of at least one cyano group-containing monomer. U.S. Pat. No. 5,093,254 teaches a method for separating proteins using a liquid two-phase protein extraction system, the lighter upper phase of which has polyvinylpyrrolidone and a heavier lower phase of maltodextrin. U.S. Pat. No. 5,089,470 teaches a method for removing heavy metals from an aqueous solution in which the aqueous solution is contacted with a solid substance comprising a water-insoluble polymeric material to which is attached molecules of polyglycines for a time period effective for the metals to become attached to the polyglycines and, having been depleted of metals, separated from the solid substance. U.S. Pat. No. 4,981,961 teaches a method and compositions for separation and purification of proteins and other organic molecules using synthetic affinity ligands in which a reactive derivative of a polymeric carrier is formed by reacting the polymer with a substituted 2-halopyridine and then reacting the activated polymer with a ligand containing one or more nucleophilic groups to form a coupled product. U.S. Pat. No. 4,276,179 teaches a process for removing non-polymeric halogenated hydrocarbons and molecular and elemental halogens from an aqueous media in which the aqueous media is contacted with polyolefinic microporous adsorbent having a surface area of from about 10 to about 40 square meters per gram of adsorbent. U.S. Pat. No. 4,230,053 teaches a method of disposing of toxic material, such as PBB, by thermal means, namely combustion.

U.S. Pat. No. 4,629,785 teaches the extraction of nutritious materials from waste solids such as waste activated sludge by converting active bacteria in the sludge to an inactive form using physical means, subjecting the sludge to an adsorbent material capable of adsorbing the nutritious materials in an uncharged state from the sludge, extracting the nutritious material from the adsorbent material by contacting it with an alkaline material having a cationic species to form a mixture of said separated nutritious material and the alkaline material, and separating the nutritious material and the cationic species and other cations by contacting the mixture with a cation exchange resin.

It is also known that proteins can be imprinted to create specific adsorbents for a variety of molecules. Such imprinting is taught by Dabulis, K. et al., "Molecular Imprinting of Proteins and Other Macromolecules Resulting in New Adsorbents", *Biotechnology and Bioengineering*, Vol. 39, pages 176–185 (1992), John Wiley and Sons, Inc., in which bovine serum albumin (BSA) was imprinted to create an affinity for L-malic acid, a polyfunctional organic molecule, in ethel acetate and other anhydrous solvents. The mechanism of imprinting and binding was indicated to involve a multipoint hydrogen bonding in water of each ligand molecule of L-malic acid with two or more sites on a polymeric chain, thereby folding a segment of the polymeric chain into a cavity around the ligand. U.S. Pat. No. 5,110,833 teaches a method of preparing synthetic enzymes and synthetic antibodies using molecular imprinting in which the print molecule and a plurality of monomers are prearranged and allowed to develop complementary non-covalent or reversible covalent interactions, forming a print molecule-monomer complex. Polymerization is performed around the print molecule-monomer complex and the print molecule is removed from the polymer by extraction, thereby creating a cavity in the polymer corresponding to the print molecule. Polymerization thus preserves the complementarity to the print molecule and the polymer produced in this manner selectively adsorbs the print molecule which binds more favorably to the extracted polymer than do structural analogues. However, this method is applicable generally to a single print molecule and thus would not produce a polymer capable of binding all of the components of a mixture containing a plurality of congeners.

None of the prior art known to me teaches or suggests biosorbents, or sorbents of any kind, capable of binding all of the components of a PCB mixture, of which, as previously stated, there are 209 possible congeners. Although imprinting proteins is known, its use with complex mixtures of substrates or halogenated substrates of any kind is not known. In addition, known imprinting methods rely on hydrogen bonding, ionic bonding, or structural (lock and key) binding of ligand to sorbent. Imprinting which depends on the interaction of hydrophobic regions of proteins with PCB's which are hydrophobic are not taught by the prior art. Finally, to my knowledge, the direct binding of PCB's using imprinted proteins within contaminated pipelines is unknown.

SUMMARY OF THE INVENTION

It is an object of this invention to provide a method for producing biosorbents which selectively adsorb PCB's.

It is yet another object of this invention to provide a method for producing biosorbents which selectively adsorb PCB's, which method utilizes inexpensive protein sources such as activated waste sludge, food plant waste, dairy industry waste or other proteinaceous waste.

It is another object of this invention to provide a method for using biosorbents to remove PCB's from contaminated oil.

It is yet another object of this invention to provide a method for removing PCB's from oils found in gas distribution pipelines.

It is yet another object of this invention to provide a method for producing biosorbents capable of directly binding the full array of PCB congeners.

These and other objects of this invention are achieved in accordance with one embodiment of the method of this invention in which at least one proteinaceous material is contacted with a molar excess of a PCB mixture comprising at least one PCB congener to form a protein/PCB congener mixture. The molar ratio of the PCB mixture to the proteinaceous material is preferably in the range of about 5 to 1 to about 10,000 to 1. The protein/PCB congener mixture is reduced to dryness to produce a dried protein/PCB congener mixture. The PCB congeners in said dried protein/PCB congener mixture are extracted from the mixture leaving a biosorbent in the form of an imprinted protein. In a preferred embodiment of the process of this invention, the protein/PCB congener mixture is freeze dried to produce a freeze dried protein/PCB congener mixture from which the PCB congeners are extracted.

In accordance with one embodiment of this invention, the PCB congeners are extracted from the dried protein/PCB congener mixture using at least one anhydrous organic solvent. In a preferred embodiment of this invention, the anhydrous organic solvent is selected from the group consisting of acetone, hexane, dichloromethane, mineral oil, diesel oil, ethanol, and mixtures thereof.

In accordance with another embodiment of this invention, the biosorbent is physically affixed to a support material, such as plastic beads or a fibrous material. To selectively remove PCB's from a contaminated environment such as oils in a gas distribution pipeline, the biosorbent need merely be brought in contact with the PCB contaminated oil. In a particularly preferred embodiment, the fibrous material supporting the biosorbent is in the form of a mop and is attached to a "pig", that is, a motorized vehicle, which is capable of travelling within gas distribution pipelines. Thus, as the pig is guided through the contaminated pipelines, the PCB biosorbent containing mop selectively attracts PCB's within the contaminated gas pipeline. Upon retrieval of the pig, the PCB's are eluted from the mop using an anhydrous organic solvent, such as dichloromethane, thereby enabling reuse of the mop to treat additional lengths of pipeline. The eluted PCB's which are now in a concentrated form can either be destroyed or sent for disposal. In accordance with yet another embodiment of this invention, the proteinaceous material is affixed to said support material after which it is imprinted with PCB's in accordance with the method of this invention for imprinting proteins to selectively adsorb PCB's.

In accordance with one embodiment of this invention, each of the steps of the method of this invention is carried out at ambient temperature and pressure.

DESCRIPTION OF PREFERRED EMBODIMENTS

A critical feature of the molecular imprinting process in accordance with this invention is the creation of a biosorbent capable of adsorbing a broad range of PCB congeners, of which there are a possible 209, compared to known processes which produce biosorbents capable of selectively adsorbing only a limited array of molecules as a consequence of imprinting using a single molecular structure. Among the 209 PCB congeners are structures so diverse that they behave differently chemically such that imprinting with a single molecule could not produce imprinted proteins which perform effectively to bind all PCB structures. One reason for this distinction between known molecular imprinting processes and the method of this invention is the fact that known molecular imprinting processes generally rely on non-covalent interactions between the imprinted material and the imprinted molecule. Such interactions include ionic interactions, hydrogen bond exchanges, and dipole—dipole interactions. Such interactions normally occur between molecules having functional groups such as —OH, —SH, —NH$_2$, —COOH, and other groups. PCB's, by comparison, have no functional groups of this kind and thus the basis for molecular imprinting is different than taught by known protein imprinting processes.

It will be apparent to those skilled in the art that any protein can be used in accordance with a process of this invention for imprinting to create adsorbents having a selectivity for all PCB congeners. However, in accordance with one embodiment of this invention, it is preferred that hydrophobic proteins be used for imprinting of PCB's. The use of hydrophobic proteins promotes diffusion of the PCB's through the protein material into the cavities therein created by the imprinting process during adsorption of the PCB's from the PCB contaminated substances. Moreover, the hydrophobic regions of the proteins preferentially interact with the PCB's during the imprinting process. In addition, it is known that exposure of an imprinted protein to water results in substantial loss of "imprint memory", thereby reducing the affinity of the biosorbent for the selective adsorption of the imprinted molecule. However, the use of hydrophobic proteins may provide some immunity to loss of memory during the adsorption process if the protein comes in contact with water.

In accordance with one embodiment of the process of this invention, inexpensive proteins, such as activated waste sludge, food plant waste, dairy industry waste, and other materials containing hydrophobic proteins are treated to produce the hydrophobic protein material to be imprinted. In accordance with a preferred embodiment of this invention, the protein used is lipase. PCB's, extracted from a contaminated oil, are purified and mixed with lipase at a molar ratio of about 1,000 to 1 in an aqueous solution, an aqueous/solvent mixture or an anhydrous solvent. During imprinting, volatile solvents that solubilize PCB's, thereby promoting more efficient contact between the PCB's and the protein to be imprinted, and that can subsequently be easily removed by volatilization and/or freeze drying leaving only the PCB's in the final stages of the imprinting process are preferred. Suitable solvents include ethanol, methanol, chloroform, carbon tetrachloride, dichloromethane, acetane, hexane and ether. It will be apparent to those skilled in the art that there exists other such solvents which are suitable for use in this process. The resulting lipase/PCB congener mixture is reduced to dryness by removing all water and/or volatile solvents. Freeze drying or evaporative drying by conventional means can be used after which the PCB's are removed from the imprinted lipase using dichloromethane, forming PCB imprinted lipase.

In accordance with one embodiment of this invention, the imprinted lipase is physically affixed on a plurality of thin plastic fibers which are formed into a mop and affixed to a motorized "pig", or remote control vehicle, capable of travelling within a gas distribution pipeline. The pig, having been outfitted with the PCB biosorbent mop, is passed through the PCB contaminated pipes and retrieved. The PCB's adsorbed by the biosorbent from PCB contaminated oil present within the pipes are eluted from the mop using dichloromethane, rendering the mop reusable for treatment of additional length of pipeline. The eluted PCB's, now in a concentrated form, can either be destroyed or sent for disposal. It will be apparent to those skilled in the art that the biosorbent may be physically affixed to numerous substrate materials including plastic filaments or beads and other suitable materials depending upon the application. Physically affixing imprinted proteins to solid supports can be accomplished by numerous means such as entrapment by including the imprinted proteins in a gel or plastic polymerization reaction, physical localization by fiber entrapment, by covalent bonding methods such as the use of cyanogen bromide, diazotization, or arylation, or by a variety of other methods well known in the art. See, for example, "Manual of Industrial Microbiology and Biotechnology", A. L. Demain & N. A. Solomon eds., 1986, American Society for Microbiology Press, Washington, D.C., pp. 230–247.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principals of the invention.

I claim:

1. A method for selective adsorption of PCBs comprising the steps of:

mixing at least one proteinaceous material with a molar excess of at least one PCB congener mixture forming a protein/PCB congener mixture;

drying said protein/PCB congener mixture;

extracting each of said PCB congeners from said dried protein/PCB congener mixture forming a biosorbent in the form of an imprinted protein; and contacting a PCB-containing environment with said imprinted protein resulting in selective adsorption of said PCBs.

2. A method for selective adsorption of PCB's in accordance with claim 1, wherein said protein/PCB congener mixture is freeze dried.

3. A method for selective adsorption of PCBs in accordance with claim 1, wherein said biosorbent is disposed on a support material.

4. A method for selective adsorption of PCBs in accordance with claim 3, wherein said support material is one of plastic filaments and plastic beads.

5. A method for selective adsorption of PCBs in accordance with claim 1, wherein said PCBs are eluted from said biosorbent.

6. A method for selective adsorption of PCBs in accordance with claim 5, wherein said PCBs are eluted with a solvent selected from the group consisting of dichloromethane, carbon tetrachloride, chloroform, diesel oil, ethanol, and mixtures thereof.

7. A method for selective adsorption of PCBs in accordance with claim 1, wherein said PCB congeners are extracted from said dried protein/PCB congener mixture using at least one anhydrous organic solvent.

8. A method for selective adsorption of PCBs in accordance with claim 7, wherein said anhydrous organic solvent is selected from the group consisting of acetone, hexane, dichloromethane, mineral oil, diesel oil, ethanol, and mixtures thereof.

9. A method in accordance with claim 1, wherein each of said steps is carried out at ambient temperature and pressure.

* * * * *